(12) United States Patent
Bowker

(10) Patent No.: US 11,497,687 B2
(45) Date of Patent: Nov. 15, 2022

(54) CHROMIC COMPOSITIONS

(71) Applicant: Theunseen Limited, London (GB)

(72) Inventor: Lauren Bowker, London (GB)

(73) Assignee: Theunseen Limited, London (GB)

( * ) Notice: Subject to any disclaimer, the term of this patent is extended or adjusted under 35 U.S.C. 154(b) by 9 days.

(21) Appl. No.: 16/626,085

(22) PCT Filed: Jun. 22, 2018

(86) PCT No.: PCT/EP2018/066723
§ 371 (c)(1),
(2) Date: Dec. 23, 2019

(87) PCT Pub. No.: WO2018/234530
PCT Pub. Date: Dec. 27, 2018

(65) Prior Publication Data
US 2020/0206096 A1 Jul. 2, 2020

(30) Foreign Application Priority Data
Jun. 22, 2017 (GB) .................................. 1709992

(51) Int. Cl.
*A61K 8/02* (2006.01)
*A61K 8/11* (2006.01)
*A61K 8/34* (2006.01)
*A61K 8/81* (2006.01)
*A61Q 5/06* (2006.01)

(52) U.S. Cl.
CPC .............. *A61K 8/0295* (2013.01); *A61K 8/11* (2013.01); *A61K 8/345* (2013.01); *A61K 8/8152* (2013.01); *A61K 8/8164* (2013.01); *A61K 8/8176* (2013.01); *A61Q 5/065* (2013.01); *A61K 2800/412* (2013.01); *A61K 2800/438* (2013.01)

(58) Field of Classification Search
CPC ....................................................... A61K 7/00
USPC ....................................................... 424/402
See application file for complete search history.

(56) References Cited

U.S. PATENT DOCUMENTS

| | | | |
|---|---|---|---|
| 4,288,622 A | 9/1981 | Kalopissis et al. | |
| 4,301,023 A * | 11/1981 | Schuberth | A61K 8/0295 252/299.7 |
| 4,904,563 A * | 2/1990 | Aoai | B01J 13/025 428/402.2 |
| 4,920,991 A | 5/1990 | Shibahashi et al. | |
| 5,705,093 A * | 1/1998 | Coates | C09K 19/46 252/299.01 |
| 6,027,537 A | 2/2000 | Leduc et al. | |
| 6,270,783 B1 * | 8/2001 | Slavtcheff | A61K 8/0208 424/10.1 |
| 6,531,118 B1 | 3/2003 | Gonzalez et al. | |
| 7,942,937 B2 | 5/2011 | Brun | |
| 2001/0014341 A1 | 8/2001 | Lemann et al. | |
| 2002/0122780 A1 | 9/2002 | McManus et al. | |
| 2002/0192247 A1 | 12/2002 | Theisen | |
| 2003/0082121 A1 | 5/2003 | Borsakian et al. | |
| 2006/0008433 A1 | 1/2006 | Chevalier | |
| 2007/0142263 A1 | 6/2007 | Stahl et al. | |
| 2007/0261179 A1 | 11/2007 | Dorkel et al. | |
| 2008/0241086 A1 | 10/2008 | Thevenet | |
| 2009/0151086 A1 | 6/2009 | Brun | |
| 2012/0308497 A1 | 12/2012 | Lee | |
| 2015/0328138 A1 | 11/2015 | Lo et al. | |
| 2016/0220454 A1 | 8/2016 | Sanders | |

FOREIGN PATENT DOCUMENTS

| | | |
|---|---|---|
| DE | 19847883 A1 | 4/2000 |
| DE | 10219296 A1 | 11/2003 |
| EP | 0359909 A2 | 3/1990 |
| EP | 0617730 B1 | 10/1994 |
| EP | 1532970 A2 | 5/2005 |
| EP | 2070516 B1 | 8/2013 |
| FR | 2928267 A1 | 9/2009 |
| GB | 227784 A | 5/1925 |
| GB | 1227784 A1 | 4/1971 |
| JP | 0182808 U | 6/1989 |
| JP | 2001122741 A | 5/2001 |
| JP | 2003128932 A | 5/2003 |
| JP | 2008208287 A | 9/2008 |
| KR | 2002007519 | 9/2002 |
| WO | 2016198784 A1 | 12/2016 |

OTHER PUBLICATIONS

Dawson, Timothy L., Changing colours: now you see them, now you dont, Coloration Technology, Aug. 1, 2010, vol. 126, Nr.:4, pp. 177-188, Wiley.
International Preliminary Report on Patentability dated Dec. 24, 2019 for International Application No. PCT/EP2018/066723.
International Search Report dated Sep. 13, 2018 for International Application No. PCT/EP2018/066723.
UK Search Report dated Mar. 12, 2018 for GB Application No. GB1709992.0.

* cited by examiner

*Primary Examiner* — Walter E Webb
(74) *Attorney, Agent, or Firm* — Cook Alex Ltd.

(57) ABSTRACT

A chromic composition adapted for application to a substrate comprising a reversible colour-change composition and a binder composition is provided. The colour change composition includes a leuco-dye and/or liquid crystal. The composition may be applied to keratinous material, polymers or other substrates to provide a colour change effect and other desirable properties such as natural feel and durability.

18 Claims, 1 Drawing Sheet

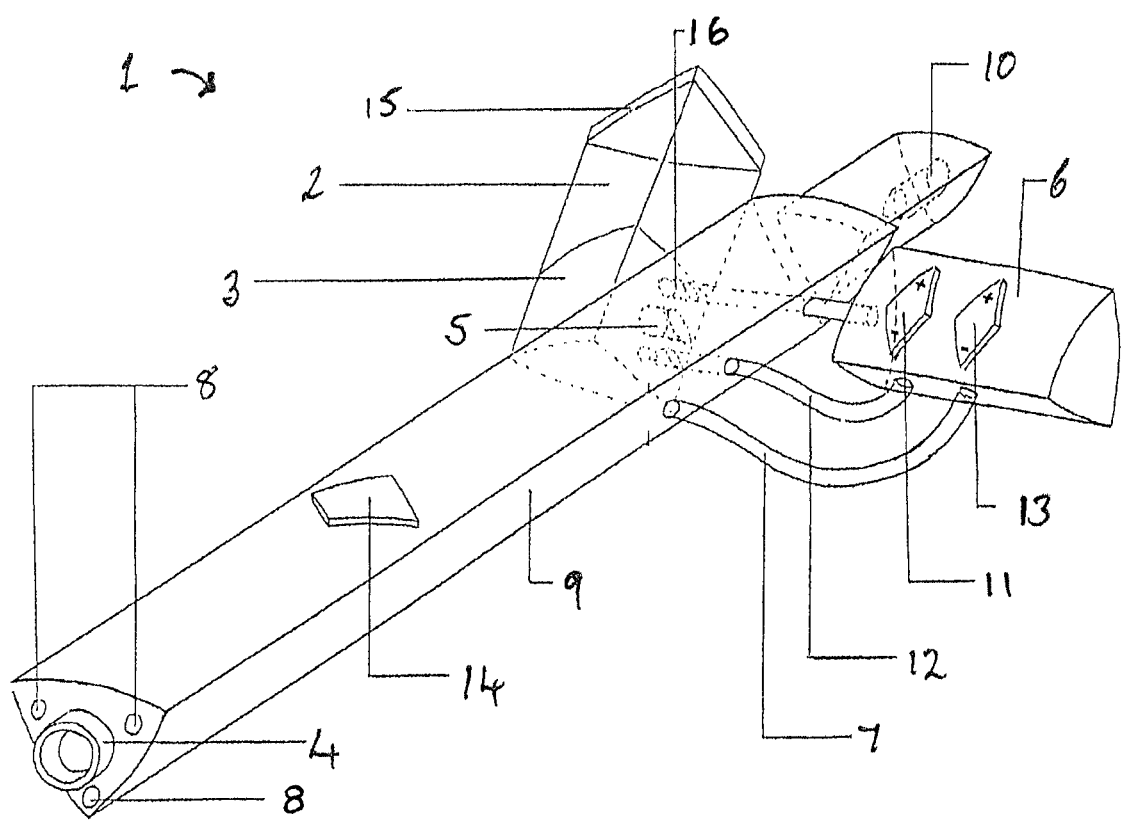

CHROMIC COMPOSITIONS

CROSS-REFERENCE TO RELATED APPLICATIONS

This is a U.S. National Stage of International PCT Application No. PCT/EP2018/066723, filed Jun. 22, 2018 which claims the benefit of and priority to Great Britain Application No. 1709992.0, filed Jun. 22, 2017, the disclosures of which are hereby incorporated by reference in their entireties.

This invention relates to a chromic composition suitable for application to a substrate to provide reversible colour-change to the substrate. In particular, the invention relates to a thermochromic colour composition comprising a colour-change compound, especially a leuco-dye and preferably a liquid crystal compound, for use in providing a colour change to a substrate according to changes in ambient or applied external conditions and especially to a hair colour-change composition.

Chromic compositions are widely known and change between a first and second coloured state, one of which may be colourless, in response to a change in an external condition such as application of energy for example through a change in temperature or pressure or incidence of light. Chromic compositions which change colour with a change in temperature are known generally as thermochromic compositions, with pressure as piezochromic compositions, and, with light, as photochromic compositions. Chromic compositions may also be referred to as colour-change or colour memory compositions.

Colour change in chromic compositions may be provided by different types of materials including leuco-dyes and liquid crystals and tailoring the composition to provide a change of colour in the desired circumstances remains a challenge.

Thermochromic compositions reversibly change colour or change between different coloured states or a coloured and colourless state when subjected to a change in temperature of a sufficient magnitude. Typically, a change in temperature will lead to a change in colour of the colour-change material. With an increase or decrease in temperature, the colour-change material will typically retain colour until a maximum temperature for retention of the complete coloured state is reached. The composition will then progressively change colour or become colourless as the temperature increases or decreases until it has completely changed colour. As the thermochromic composition cools it will reach a temperature below which the colour changes or reappears. Thermochromic materials, having standard colour change schemes and bandwidths, that is a difference in temperature at which colour change occurs from a first to a second colour and in reverse from the second colour to the first, are commercially available, for example from LCR Hallcrest.

Chromic compositions are known for use in a wide range of applications for example in toys, printed materials, decoration, writing instruments, temperature indicators in packaging of medical products such as vaccines and in industrial applications. The chromic composition must meet particular requirements or criteria for use in different applications.

Hair colouring products are known but often show irreversible colour-change and relatively low intensities of colour or pastel colours. Ultra violet (UV) fluorescent dyes are also known and typically reflect incident UV light into a longer wavelength in the visible spectrum.

We have now found that by employing a binder system which has been tailored and adapted to a particular substrate, an attractive aesthetic effect, in particular excellent surface reflection, providing intense colours, contrast between different colours and responsive colour change and adherence to the substrate and other desirable characteristics may be secured.

The invention provides in a first aspect a chromic composition product adapted for application to a substrate comprising a reversible colour-change composition and a binder composition comprising a fixative, a carrier and optionally a rheology modifier, wherein the fixative comprises a polymer having one or more monomeric units selected from acrylic acid, methacrylic acid, hydroxyethyl methacrylic acid, alkyl preferably $C_1$ to $C_4$, methacrylic acid, alkyl preferably $C_1$ to $C_4$, acrylic acid, alkyl preferably $C_1$ to $C_4$, amino acrylic acids, esters of any such acrylic or methacrylic monomers and ethers of any such acrylic or methacrylic monomers, acrylated dimethiconol, alkyl, preferably $C_2$ to $C_8$, amide, polyethylene glycol, polypropylene glycol, polybutylene glycol, $C_2$ to $C_4$ alkylene glycols, maleic anhydride, dimethylaminopropylamine (in polyimide-1), vinyl pyrrolidone (in PVP and polyquaternium-1/11), vinyl alcohol, alkylene polyethylene glycol, alkyl $C_2$ to $C_8$, acrylamide, vinyl caprolactam, vinyl acetate, vinyl methyl ether, crotonic acid, and esters and ethers thereof and methacrylated gelatin.

Suitably, the chromic composition is a thermochromic composition, a photochromic composition or a piezochromic composition. In referring to a "colour-change" composition, we include any visual change including between clear to opaque, for example white.

Preferably the colour-change composition comprises a colour-change component selected from a leuco dye and a liquid crystal. The leuco dye or liquid crystal may be encapsulated. Where the colour-change component is encapsulated, the encapsulation suitably comprises a known encapsulation material which is compatible with the colour change component. In one embodiment, a leuco-dye colour change component is encapsulated in a melamine formaldehyde encapsulate. A liquid crystal colour change component is suitably encapsulated in a gelatin and gum arabic mixture.

Where a liquid crystal is employed, the liquid crystal may be encapsulated or a polymer dispersed liquid crystal. A polymer dispersed liquid crystal comprises a discrete phase dispersed in a continuous phase. Suitably, the discrete phase comprises the liquid crystal and the continuous phase comprises the binder composition, preferably a thermoset polymer composition.

In a preferred embodiment the colour-change component comprises at least one encapsulated liquid crystal, optionally together with an unencapsulated liquid crystal, especially where the intended substrate is hair. However, adhering an encapsulated liquid crystal to a substrate such as hair in a uniform manner to provide good colour properties and retain a pleasant "feel" to the hair and the a temporary resistance to washing presents some challenges.

Encapsulated liquid crystals are typically much larger than dyes, leuco-dyes and pigments, typically having a particle size from 5 to 50 microns, for example from 10 to 20 microns, a similar order of magnitude to hair fibres. This presents some challenges in seeking to adhere liquid crystals to hair fibres. Due to the relatively similar size of encapsulated liquid crystals and the hair fibre, a relatively thick coating is required to accommodate the encapsulate. In addition, a vibrancy of colour is aesthetically desirable but encapsulated liquid crystals may require higher loadings of encapsulate to achieve a suitable intensity or vibrancy of colour. Known hair dyeing techniques typically require a pre-treatment to lighten hair in order to obtain brighter dyed hair, for example green dye when applied to dark hair does not typically provide an acceptable colouration unless the hair is pre-lightened. However, higher loadings with attendant poor "feel" qualities and prior lightening treatments are undesirable.

A surface colour coating of an encapsulated liquid crystal may be bound to hair to provide a uniform coating by employing to provide a temporary hair colour effect with vibrant colour may be achieved without a need to lighten the hair beforehand by providing a combination of colour effect materials and a coating medium comprising a combination of components without the need to pre-lighten hair. The term "temporary" as employed means a colour composition which has resistance to standard washing, for example in a shower and according to different hair types provided that the composition may be removed by washing i.e. it is not covalently bound to the hair. Suitably, the temporary hair colour composition is tailored to be washed out after 1 or 2 washes (referred to as 'hair makeup'), after 3 to 10, for example, 6 washes (referred to as 'temporary hair colour') or after 10 or more, for example 12, washes (referred to as 'pseudo-semi-permanent').

The chromic colour change product of the invention enables an encapsulated liquid crystal component to be applied to hair, at desirable levels to provide a vibrant colour effect without compromising the feel of the substrate.

In a further embodiment the liquid crystal comprises a non-polymerisable liquid crystal. For example, the liquid crystal may be wholly a non-polymerisable liquid crystal.

Where the colour component comprises a liquid crystal, the liquid crystal may be in the form of a polymer dispersed liquid crystal (PDLC) in which the liquid crystal is present in droplets, typically of a micron scale, for example from 0.01 to 10 microns, dispersed in a continuous polymer phase.

The chromic composition may be non-iridescent or iridescent according to the desired effect. The colour-change component and the chromic composition are suitably formulated to provide a desired visual appearance on the substrate. For example, leuco dyes may be employed to provide a matt or non-iridescent appearance. Other appearances may be provided, for example pearlescent, gloss and iridescent.

Preferably, the colour-change component comprises an encapsulated leuco dye, an encapsulated liquid crystal or a PDLC liquid crystal. Advantageously, PDLC liquid crystals may provide iridescent qualities as well as a colour-change properties.

In one embodiment, the invention provides an iridescent chromic composition product adapted for application to a substrate comprising a reversible colour-change composition comprising a polymer dispersed liquid crystal and a binder composition comprising a fixative, a carrier and optionally a rheology modifier, wherein the fixative comprises a polymer having one or more monomeric units selected from acrylic acid, methacrylic acid, hydroxyethyl methacrylic acid, alkyl preferably $C_1$ to $C_4$, methacrylic acid, alkyl preferably $C_1$ to $C_4$, acrylic acid, alkyl preferably $C_1$ to $C_4$, amino acrylic acids, esters of any such acrylic or methacrylic monomers and ethers of any such acrylic or methacrylic monomers, acrylated dimethiconol, alkyl, preferably $C_2$ to $C_8$, amide, polyethylene glycol, polypropylene glycol, polybutylene glycol, $C_2$ to $C_4$ alkylene glycols, maleic anhydride, dimethylaminopropylamine (in polyimide-1), vinyl pyrrolidone (in PVP and polyquaternium-1/11), vinyl alcohol, alkylene polyethylene glycol, alkyl $C_2$ to $C_8$, acrylamide, vinyl caprolactam, vinyl acetate, vinyl methyl ether, crotonic acid, and esters and ethers thereof and methacrylated gelatin.

The invention provides in a second aspect a method of providing a reversible colour-change substrate comprising applying to a substrate a chromic product comprising a reversible colour-change composition and a binder composition comprising a fixative, a carrier and optionally a rheology modifier, wherein the fixative comprises a polymer having one or more monomeric units selected from acrylic acid, methacrylic acid, hydroxyethyl methacrylic acid, alkyl preferably $C_1$ to $C_4$, methacrylic acid, alkyl preferably $C_1$ to $C_4$, acrylic acid, alkyl preferably $C_1$ to $C_4$, amino acrylic acids, esters of any such acrylic or methacrylic monomers and ethers of any such acrylic or methacrylic monomers, acrylated dimethiconol, alkyl, preferably $C_2$ to $C_8$, amide, polyethylene glycol, polypropylene glycol, polybutylene glycol, $C_2$ to $C_4$ alkylene glycols, maleic anhydride, dimethylaminopropylamine (in polyimide-1), vinyl pyrrolidone (in PVP and polyquaternium-1/11), vinyl alcohol, alkylene polyethylene glycol, alkyl $C_2$ to $C_8$, acrylamide, vinyl caprolactam, vinyl acetate, vinyl methyl ether, crotonic acid, and esters and ethers thereof and methacrylated gelatin.

In a further aspect, the invention provides the use of a chromic product comprising a chromic reversible colour-change composition and a binder composition in coating or dying a substrate to provide a reversible colour-change effect on the substrate wherein the binder comprises a fixative, a carrier and optionally a rheology modifier, wherein the fixative comprises a polymer having one or more monomeric units selected from acrylic acid, methacrylic acid, hydroxyethyl methacrylic acid, alkyl preferably $C_1$ to $C_4$, methacrylic acid, alkyl preferably $C_1$ to $C_4$, acrylic acid, alkyl preferably $C_1$ to $C_4$, amino acrylic acids, esters of any such acrylic or methacrylic monomers and ethers of any such acrylic or methacrylic monomers, acrylated dimethiconol, alkyl, preferably $C_2$ to $C_8$, amide, polyethylene glycol, polypropylene glycol, polybutylene glycol, $C_2$ to $C_4$ alkylene glycols, maleic anhydride, dimethylaminopropylamine (in polyimide-1), vinyl pyrrolidone (in PVP and polyquaternium-1/11), vinyl alcohol, alkylene polyethylene glycol, alkyl $C_2$ to $C_8$, acrylamide, vinyl caprolactam, vinyl acetate, vinyl methyl ether, crotonic acid, and esters and ethers thereof and methacrylated gelatin.

The colour-change effect may be tailored to provide a colour change under prescribed external conditions such as prevailing ambient temperature in different seasons or localities or in response to warmth or pressure provided by touch for example hand touch, or to change colour as a result of light or aerodynamic flow across the substrate.

Advantageously, compositions according to the invention provide accurate colour matching, that is by matching a colour with a pre-determined reference colour, for example a catalogue colour or pantone and provide a high intensity colour and provide durability in that they remain on or impregnated within the substrate for a suitable period or a certain number of wash cycles.

The properties of the colour-change composition may be tailored according to the intended field of use by appropriate selection of the components of the binder composition having regard to the substrate to which the composition is to be applied. The chromic composition is suitable for application to an organic or inorganic substrate which may be a natural polymer or natural protein for example cotton yarn, jute, silk, natural rubber, wool, starch and the like, a synthetic polymer and keratinous tissue.

Application to keratinous material, for example hair, may require the composition to have certain tactile properties such that it is pleasant or not irritating for the wearer and tactile and suitably feels natural to touch. Desirably, the composition or the substrate to which the composition is applied does not form clumps or lead to other characteristics which are disadvantageous or undesirable as regards visual or tactile impact.

Application to a fabric, leather or metal may require the composition to be particularly durable and resistant to physical abrasion whilst providing aesthetically desirable colour-change.

The composition may be fluorescent, particularly with incident light near the UV spectrum, and desirably iridescent. Iridescence suitably provides scattering of incident light to provide a shimmering effect of multiple colours or a rainbow of colours and arises due to composition of the invention forming a film or coating when applied to a substrate and having suitable refractive characteristics. The chromic composition may be applied to the substrate by a film or coating forming process, by for example spraying, dyeing, screen-printing.

The composition may be tailored to provide a desired visual appearance for particular circumstances or moods and adapted to provide a faster or slower colour change with single or multiple colour change within a bandwidth of temperatures or other external parameters.

The chromic composition comprises a binder composition which acts as a carrier for the chromic composition and aids deposition on or impregnation into the substrate and a reversible colour-change composition. The colour-change composition may be encapsulated.

The colour change composition is suitably present in the chromic composition at a level of 10 to 90%, preferably 25 to 70%, more preferably 35 to 60%, especially 40 to 55% by weight. The binder composition is suitably present in the chromic composition at a level of 90 to 10%, preferably 70 to 25%, more preferably 60 to 35%, especially 55 to 40% by weight.

The colour-change composition may comprise colour-change components which change colour upon a change of temperature, change of pressure or change of incident light. Changing ambient conditions or artificially applied changes in conditions may instigate colour-change.

The colour-change composition may be encapsulated as described above and comprises a colour change material, an encapsulation wall material and a carrier. The encapsulation wall material may comprise any known encapsulation material which is suitable for use in personal products for example gum arabic, gelatin, polyvinyl alcohol and melamine formaldehyde. Suitably, the wall material comprises a polymer or a combination of polymers. In one embodiment, the wall material comprises a combination of gum arabic and polyvinyl alcohol. The wall material preferably comprises from 1 to 30%, more preferably 5 to 25%, for example 8% or 20% by weight of wall material based on the weight of the colour change composition.

Where the colour component is a leuco dye, the wall material suitably comprises melamine formaldehyde. Where a liquid crystal is employed, the wall material suitably comprises gum arabic and/or a gluteraldehyde cross-linked gelatin.

The carrier for the colour-change composition may be the same or different to the carrier for the binder composition as described below. It should however be compatible with the encapsulation wall material to ensure structural integrity for the encapsulate. Preferably, the carrier for the colour-change composition comprises water and is present at a level of 30 to 80%, more preferably 50 to 70%, for example 60% by weight of the colour-change composition.

The colour change material is suitably selected from a chiral nematic liquid crystal mixture, a leucodye and combinations thereof. Combinations of leuco dyes and liquid crystals are especially suitable for providing multiple, for example 5 or 6, colour changes. Combinations of colour-change materials are suitably mixed together.

Examples of suitable leuco dyes include Benzol lecyo methylene blue ([3,7-bis(dimethylamino)phenothiazin-10-yl]-phenylmethanone), Leucomalachit Green (4-[[4-(dimethylamino)phenyl]-phenylmethyl]-N,N-dimethylaniline), Leucocrystal Violet (4-[bis[4-(dimethylamino)phenyl]methyl]-N,N-dimethylaniline), Leuco Gentian Violet-d6 (4-[[4-[bis(trideuteriomethyl)amino]phenyl]-[4-(dimethylamino)phenyl]methyl]-N,N-dimethylaniline), 4-(2,4-dinitroanilino)phenol, Leuco-indoaniline (4-[4-(dimethylamino)anilino]cyclohexa-2,5-dien-1-one), Leuco sulphur Blue 11 (disodium; 4-(2,4-dinitroanilino)phenol; sulfanide;hydroxide) and Leucoquinizarin (anthracene-1,4,9,10-tetrol).

Examples of suitable liquid crystals include cholesterol-like chiral organics, chiral nematic liquid crystals including (S)-(+)-4-cyanophenyl-4-n-2-methylbutylbiphenyl-4'-carboxylate, (S)-(+)-4-(2methylbutyl)phenyl-4-n-2-methylbutylbiphenyl-4'-carboxylate, (S)-(+)-4-hexylphenyl-4-n-2-methylbutylbiphenyl-4'-carboxylate, S-(+)-4-(2-methyl)phenyl-4-hexyloxybenzoate, (±)-4-(2-methylbutyl)phenyl-4-hexyloxybenzoate, S-(+)-(2-methylbutyl)phenyl-4-octyloxybenzoate, (±)-4-(2-methylbutyl)phenyl-4-octyloxybenzoate, S-(+)-(2-methylbutyl)phenyl-4-decycloxybenzoate, S-(+)-(2-methyl butyl)phenyl-4-dodecycloxybenzoate, (S)-(+)-4-(2-methylbutylphenyl-4-n-octylbiphenyl-4'-carboxylate, S-(+)-4-(2-methylbutyl)phenyl-4-propylbenzoate, (±)-4-(2-methylbutyl)phenyl-4-propylbenzoate, (S)-(+)-4-(2-methylbutyl)phenyl-4-n-heptylbiphenyl-4'-carboxylate, S-(+)-4-(2-methylbutyl)phenyl-4-heptylbenzoate, S-(+)-4-(2-methylbutyl)phenyl-4-nonylbenzoate, S-(+)-4-(2-methylbutyl)phenyl-4-tetradecyloxybenzoate, (S)-(+)-4-(2-methylbutyl)phenyl-4-n-pentylbiphenyl-4'-carboxylate, S-(+)-4-(2-methylbutyl)phenyl-4-(trans-4-pentylcyclohexylmethoxy)benzoate, S-(+)-4-(2-methylbutyl)phenyl-4-(trans-4-propylcyclohexyl)benzoate and (±)-4-(2-methyl butyl)phenyl-4-(trans-4-propylcyclohexyl)benzoate, S-(+)-4-(2-methylbutyl)phenyl-4-(trans-4-pentylcyclohexyl)benzoate, S-(+)-4-(2-methylbutyl)phenyl-4-(trans-4-heptylcyclohexyl)benzoate, S-(+)-4-(2-methylbutyl)phenyl-4-methoxybenzoate, S-(+)-4-2(methylbutyl)-4'cyanophenyl, 4-pentylphenyl-4-alkoxybenzoates for example 4-pentylphenyl-4-methoxybenzoate, 4-pentylphenyl-4-pentoxybenzoate, 4-pentylphenyl-4-hexoxybenzoate, 4-pentylphenyl-4-octoxybenzoate, 4-pentylphenyl-4-methylbenzoate, 4-pentyl phenyl-4-propylbenzoate and 4-pentylphenyl-4-pentylbenzoate, 4-ethylphenyl-4-ethylbenzoate, 4-(heptyloxy)benzoic acid-2fluoro-4-pentylphenyl ester The colour change material is preferably present at a level of 0.5 to 70%, 10 to 60% and especially 20 to 50%, more preferably 25 to 45% and especially 28 to 40%, for example 32% and 40% by weight of the colour-change composition. Where an encapsulated liquid crystal is present, it is suitably incorporated into the composition as a slurry of the microencapsulated liquid crystal in an aqueous slurry, preferably solely water and the encapsulate. Suitably the encapsulated liquid crystal is present in the slurry at a level of 10 to 90%, preferably 15 to 60% and especially 20 to 50% by weight of the aqueous slurry.

The colour-change composition suitably provides a wide hysteresis and a tuneable hysteresis. By varying the colour-change composition formulation the width of the hysteresis may be tailored according to the intended use of the product, allowing excellent flexibility in the design of the colour-change encapsulated composition or pigment.

The binder composition suitably provides a polymer film or coating on or in the substrate, for example hair, that has appropriate characteristics for the intended application and carries or holds the colour-change composition on or in the substrate. Preferably, the film has a uniform thickness upon application to the substrate so as to enable maximum reflectance of incident light on the substrate enhancing colour intensity and vibrancy.

Preferably, the binder composition is transparent.

The binder composition is suitably substantially free of silicones and silicone-containing components, especially where the colour-change component comprises an encapsulated liquid crystal.

When applied to fibrous material, for example natural hair or synthetic hair, the binder composition suitably feels natural to touch, keeps the shine of the hair intact, binds to the hair, and does not allow the hairs to bind together. The binder composition may be formulated to provide different levels of durability according to the application.

When applied to keratinous material, the composition may suitably have a resistance to standard washing, for example in a shower and according to different hair types. The binder composition may be intended to allow the chromic composition to be washed out after 1 or 2 washes (referred to as 'hair makeup'), after 3 to 10, for example, 6 washes (referred to as 'temporary hair dye') or after 10 or more, for example 12, washes (referred to as 'pseudo-semi-permanent').

The binder composition suitably has pH of 3 to 8, preferably 3 to 7.5.

The binder composition suitably comprises a fixative, a rheology modifier, a carrier and optionally a pH modifier. Suitably, the fixative is film-forming such that the chromic composition is coatable onto the substrate. The term "film-forming", refers to the property of being able to form a continuous film and adhere to a substrate, especially to keratin materials for example to hair.

In one embodiment, the chromic composition comprises a non-polymerisable liquid crystal and a non-polymerisable binder composition. In another embodiment, the composition comprises a non-polymerisable liquid crystal, encapsulated liquid crystal or PDLC, and a polymerisable binder composition which comprises a rheology modifier. Where the liquid crystal is unsealed, the colour change composition suitably comprises an unencapsulated oil and a photopolymerisable resin. Where a photopolymerisable resin is employed, the chromic composition further comprises a photoinitiator.

The fixative is preferably a polymeric fixative, which enables the composition to be applied to the intended substrate but which does not impart physical properties to the substrate when applied in use which are undesirable or incompatible with the intended final use. Where the chromic composition is to be applied to hair, it is important that the feel of the product in the hair not be too stiff for example.

In a preferred embodiment, the fixative comprises an alkyl, for example ethyl, ester of a copolymer of vinyl methyl ether and maleic anhydride or maleic acid Suitably, the fixative is present in the binder a composition at a level of 5 to 30%, preferably 10 to 25%, more preferably 12 to 20%, for example 13% and 15% by weight of the binder composition. The fixative is preferably dissolved or dispersed in the carrier.

The carrier comprises one or more dermatologically acceptable solvents. Examples of suitable solvents include alcohols, water, esters, ketones, aldehydes, ethers and hydrocarbons. Preferably, the carrier comprises water and alcohol, suitable examples of which include ethanol, propanol and butanol. Where the carrier comprises two solvents, for example alcohol and water, the ratio of the two solvents by weight is suitably 1:5 to 5:1, preferably 1:3 to 3:1 and more preferably 1:2 to 2:1.

The carrier is suitably present at a level from 30 to 95%, preferably 50 to 90%, more preferably 60 to 85% for example 80% by weight of the binder composition.

In one embodiment, the carrier comprises 45% ethanol and 35% water by weight of the binder composition and the binder composition comprises 50% by weight of the chromic colour composition.

Optionally, the binder composition also comprises a rheology modifier to aid dispensability of the chromic composition especially if the composition is to be applied as a spray and to ensure droplet size is optimal to avoid separation of components under shear during spraying and to avoid too thick a viscosity. Rheology modifiers known for use in personal care products may be employed in the binder composition.

The rheology modifier may comprise a natural thickener, a synthetic thickener and/or a dispersant or surfactant. Any known thickeners or surfactants suitable for use in the intended field of use of the composition may be employed.

Examples of natural thickeners include egg yolk, starch, cellulose, alginate, chitosan, agar, arrowroot, carrageenan, collagen, gelatin, guar gum, pectin and xantham gum.

Examples of synthetic thickeners include alkali-swellable emulsions (ASEs), hydrophobically modified alkali-swellable emulsions (HASEs) and hydrophobically ethoxylated urethane resins (HEURs).

Examples of preferred dispersants or surfactants include polysorbate 20/80, glyceryl cocoate, capryl/yl glucoside. The dispersant or surfactant may also provide a foaming function where desired, for example in the formulation of a mousse.

In one embodiment, the rheology modifier comprises a glycol, preferably selected from polyethylene glycol, polypropylene glycol, polybutylene glycol and a $C_2$ to $C_4$ alkylene glycol, for example PEG 32 and propylene glycol. The rheology modifier, if present, is suitably present at a level of 0.1 to 20%, preferably 1 to 10% for example 7% by weight of the binder composition.

Optionally, the binder composition also comprises a pH modifier and may act to provide a higher alkalinity or acidity. A pH modifier may be required depending on the polymer employed for the fixative in order to ensure the fixative does not adversely disrupt the encapsulation wall of the colour-change composition. pH modifiers known for use in personal care products may be employed in the binder composition.

Examples of alkaline the pH modifiers include comprises an aminated alcohol, for example aminomethyl propanol and triethanolamine which may also provide a foam stabilizer or surfactant function. Examples of acidic pH modifiers include citric acid and sodium gluconate, which may also provide a humectant function.

The pH modifier, if present, is suitably present at a level of 0.1 to 10%, preferably 0.5 to 5% for example 3% by weight of the binder composition.

The binder composition may also comprise a preservative such as a natural or synthetic antimicrobial. Examples of natural antimicrobials include, carylyl glycol, tea tree oil, potassium sorbate and sorbic acid. Examples of synthetic antimicrobials include phenoxyethanol, benzylalcohol and gluconolactone.

Where the colour change component is a PDLC, the binder composition suitably also comprises a photoinitiator. Examples of suitable photoinitiators include ethyl-4-(dimethylamino)benzoate, isoamyl 4-(Dimethylamino)benzoate and IRGACURE 2959.

The binder composition may also comprise a plasticiser, with known commercially available plasticisers being suitable.

The composition may also comprise a perfume, especially if the composition is intended for use on the human or animal body. Examples of suitable perfumes include peppermint oil, sweet orange essential oil, menthol, linalool, partum, methyl butyrate, citral, myrcene, limonene and eucalyptol.

Where the colour change composition is formulated as a spray, the composition may be dispensed from a non-pressurised container or from a pressurised container using a propellant. Any known propellants may be used which are suitable for the intended application, for example butane, carbon dioxide, ethane and dimethyl carbonate.

The chromic colour product may further comprise a dye. The dye may be incorporated into the colour change composition as a solution of the dye at any desired level. The dye solution may comprise 0.1 to 10% aqueous solution of the dye. The dye solution may be incorporated into the composition at a level dependent on the concentration of the dye solution and the desired final content of the dye in the composition. For example a 1% solution of the dye may be included at a level of 1 to 20%, preferably 5 to 15% for example 10% by weight of the composition.

Any dyes suitable for use in hair or cosmetic products may be employed including the following used in combination or on their own; N,N-Bis(2-Hydroxyethyl)-2-Nitro-p-Phenylenediamine, 4-Amino-3-Nitrophenol, 4-Hydroxypropylamino-3-Nitrophenol, Hydroxyethyl-2-nitro-p-toluidine, HC Blue No. 12, 3-Nitro-p-Hydroxyethylaminophenol, 2-Amino-6-Chloro-4-Nitrophenol, Acid Red 33, HC Yellow No. 2, HC ORANGE NO. 1, HC YELLOW NO. 13, Basic Yellow 57, HC Red No. 3, Basic Red 76, Basic Red 51, Acid Red 92, Basic Yellow 87, Basic Orange 31, BASIC VIOLET 2, HC Blue No. 16, Acid Violet 43, Basic Brown 17 and dyes provided by Sensient® Cosmetic technologies; Arianor Jade Blue (HC Blue 15), Covalumine fire red AS (CI 15850, Alumina, Triethoxycaprylylsilane), Noir W 699 (CI 20470, Sodium Sulfate), Covalumine astral blue (CI 42090, Alumina, Triethoxycaprylylsilane), Unipure white LC986 FSP (CI 77891, Perfluorooctyl Triethoxysilane, Polyperfluoromethylisopropyl Ether), Unipure red LC3071 (CI 15850, Aluminum Hydroxide), Unipure white LC987 GCA (CI 77891, Sodium Cocoyl Glutamate, Cystine, Lauroyl Arginine), Covarine white WN9787 (CI 77891, Aqua, Glycerin, Xanthan Gum, Sodium Citrate), Covapate Uniwhite LC 9781 (Ricinus Communis (Castor) Seed Oil, CI 77891, Polyhydroxystearic Acid), Unipure white LC981 SGP (CI 77891, Sodium Glycerophosphate), Vert covasol W7035 (CI 19140, CI 42090), unipure yellow LC182 ADT-C (CI 77492, Isopropyl Titanium Triisostearate, Bis-PEG-15 Dimethicone/IPDI Copolymer, PEG-2 Soyamine), unipure black LC989 ADT-C (CI 77499, Isopropyl Titanium Triisostearate, Bis-PEG-15 Dimethicone/IPDI Copolymer, PEG-2 Soyamine), unipure black LC988 FSP (CI 77499, Perfluorooctyl Triethoxysilane, Polyperfluoromethylisopropyl Ether), phat black DC 9206 (mixture of CI61565, CI60725, basic brown 16, acid violet 43, basic red 76, CI 26100), Arianor flash deep black (Basic Blue 99, Basic Brown 16, Acid Violet 43, Basic Red 76, Basic Yellow 57, Basic Brown 17, Polyquaternium-37, Hydrolyzed Yeast Protein)

The invention provides the use of a composition as a colour-change product on an organic substrate, particularly where the substrate is keratinous tissue of a living body, particularly a human being.

The present composition is suitable for application for cosmetic application to the living body and is formulated to pass toxicology standards for use in the cosmetics industry.

The invention further provides a cosmetic product comprising a cosmetic composition and a chromic composition according to the invention. The cosmetic composition and the chromic composition are suitably mixed or blended together to provide the cosmetic product.

Chromic compositions according to the invention are especially suitable for use as a hair colour-change composition. The composition may be applied to natural hair, to artificial hair, for example hair extensions, or both.

The composition may be formulated to provide multiple colour changes colour changes. The colour changes may occur in a desired sequence of particular colours by suitable selection of thermochromic dyes. Suitably, the composition provides two to six colour changes, respectively referred to as dichromic, trichromic, tetrachromic, pentachromic and hexachromic, with each colour change occurring at a different temperature.

The chromic composition may comprise a single colour liquid crystal which may exist in in a coloured or colourless form depending on prevailing conditions and in the latter case, show the underlying colour of the substrate. The substrate suitably has its own colour which may be the natural colour of the substrate or an artificial or applied colour, for example a dye.

The chromic composition is suitably applied as a coating to or impregnated in the substrate such that when the chromic composition is in its colourless form, the underlying colour of the substrate is visible to the observer. By employing appropriate dyes to the substrate and tailoring the chromic composition to the desired application, the appearance of the substrate as regards the underlying colour and the coloured state may be finely tuned according to the desired application.

The temperature at which a colour change occurs may be at ambient or a lower or higher temperature. Where the composition provides multiple colour-changes, the composition is suitably formulated to provide the colour-change at a desired temperature depending on the intended aesthetic effect.

Examples of desirable colour change sequences for a thermochromic composition applied to a substrate, for example human hair, and the temperatures at which the colour change occurs are set out below:
  a. Tetrachromic (four colours):
    i. 15° C.<$T_{Sub}$<20° C.=black
    ii. 20° C.<$T_{Sub}$<23° C.=red
    iii. 23° C.<$T_{Sub}$<28° C.=orange
    iv. 30° C.<$T_{Sub}$=yellow
  b. Trichromic (three colours):
    i. 20° C.<$T_{Sub}$<23° C.=red ii. 23° C.<$T_{Sub}$<28° C.=orange
iii. 30° C.<$T_{Sub}$=yellow
c. Dichromic (two colours):
i. $T_{Sub}$<29° C.=black
ii. 29° C.<$T_{Sub}$=red
d) Pentachromic (five colours):
i) <$T_{Sub}$<26° C. yellow leuco coloured state
ii) 26° C.<$T_{Sub}$<26.5° C. red liquid crystal and leuco colourless
iii) 26.5° C.<$T_{Sub}$<27° C. green liquid crystal
iv) 27° C.<$T_{Sub}$<28° C. blue liquid crystal
v) 28° C.<$T_{Sub}$ black base colour
e) Hexachromic (six colours)
i) <$T_{Sub}$<19° C. yellow both leucos coloured
ii) 26° C.<$T_{Sub}$<26.5° C. peach one leuco coloured
iii) 26° C.<$T_{Sub}$<26.5° C. red liquid crystal and leuco colourless
iv) 26.5° C.<$T_{Sub}$<27° C. green liquid crystal
v) 27° C.<$T_{Sub}$<28° C. blue liquid crystal
vi) 28° C.<$T_{Sub}$ black base colour The composition may be formulated into any suitable product form depending on the intended application.

The composition may be formulated as a personal care product for application to keratinous tissue of the human or animal body, for example hair. Suitable forms of personal care compositions for topical application include creams, gels, lotions, emulsions, serums, colloids, solutions, suspensions, ointments, milks, sprays, capsules, tablets, liquids, sticks, solids, pastes, powders, compacts, pencils, spray-on formulations, brush-on formulations, cloths, wipes, and the like. In a preferred embodiment, the composition is formulated as a spray, for example an aerosol spray and non-aerosol spray, a paint, a hair product such as a dye, a shampoo, a conditioner, a mousse, wax, gel or solid hair product optionally dispersed or carried in a liquid, for example a "chalk", a lipstick, foundation, mascara, sunless tanner or sunscreen lotion.

The composition may be formulated for application to an inanimate man-made or natural substrate such as a fabric, woven or unwoven, leather, fibres, films and the like. The composition may also be applied to a substrate in a range of ways depending on the manufacturing process of the substrate and may include screen printing, spraying, vat dyeing and painting. The composition may be applied as a coating or film onto a substrate or may impregnate or be absorbed into the substrate as desired.

The composition is suitably dermatologically acceptable when formulated as a personal care product. Where formulated for use on or near the lips or mouth, the composition is suitably orally acceptable or ingestible.

Where the substrate is natural or artificial hair, the chromic composition is suitably formulated and applied to the hair in a conventional manner including as a spray from a spray container, as a solid, for example a hair chalk, as a mousse or as a hair dye solution whether for professional or non-professional use or as a spray from a compressed spray applicator using a propellant. Hair dyes for professional and non-professional use are suitably applied by hand, with an applicator, for example a brush, or as a spray from a conventional spray applicator.

Where the chromic composition is to be deposited as a spray, it may be dispensed from a conventional spray bottle or air gun may be employed. Suitably, the binder composition is formulated at a viscosity of 1 to 100 cP suitable for spraying as will be understood by the skilled person so as to reduce or avoid clogging. The chromic composition suitably further comprises a dispersant or surfactant, preferably as herein described, to facilitate transport of the chromic composition under shear, without compromising the material properties or the colour intensity of the applied dye layer. The dispersant suitably comprises a surfactant which may be anionic, non-ionic or zwitterionic and any known surfactants which are compatible with the rest of the composition may be employed. In an especially preferred embodiment the surfactant is from a natural source, for example quallaja saponaria or an extract from pseudomonas or *Bacillus subtilis* cultures.

The chromic composition may be in solid form, for example a wax, powder or clay or may be in the form of a bi-phasic mixture, for example a gel, and formulated in a conventional manner for these type of products.

The chromic composition may be deposited as a 'hair chalk' comprising a solid chromic composition dispersed in a volatile liquid carrier. Suitably, hair chalk is applied to hair using a brush having a shape and size configured for use in applying a hair chalk. Suitably, the brush has a medium bristle for example Denman D81 and the bristles are relatively densely packed to enable the chalk to be evenly spread along the hair. Examples of preferred brushes include those available at http://www.sallyexpress.com/jack-dean-gentlemans-club-brush/ and http://www.sallyexpress.com/denman-d81-medium-bristle-brush/. Suitably, the bristles of the brush are not too open or widely spaced, for example a Denman D100 tunnel vent brush or a Denman D90 brush are less suitable for application of hair chalk. By selecting a brush having bristles with optimal flexibility and density, the chalk may be evenly applied to provide the desired effect whilst not giving rise to clogging or clumping.

The hair chalk is suitably applied between drying and brushing the hair and, preferably is applied multiple times, especially two to five times, for example three times. This method of application advantageously reduces the risk of the hair becoming undesirably clogged or clumped and impairing the effectiveness of the chalk colour composition.

Upon application to the hair, the volatile components evaporate to leave a solid, deposited dye. The volatile liquid carrier is selected to be compatible with the colour change composition, especially if it is encapsulated. Examples of suitable volatile liquid carriers include water, ethanol, acetone and the like. The liquid carrier evaporates upon application to leave the chromic composition as a uniform solid applied to the hair. Suitably the chromic composition has a viscosity of 10 kcP to 80 kcP.

The chromic composition may be formulated for professional use where the composition is applied in a salon environment by a professional stylist and for example may be in the form of a salon-applied gel.

The chromic composition may be formulated as a hair mousse. Typically, a mousse provides a foaming effect to allow manual application of the mousse to the hair. A mousse separates strands of hair to impregnate thicker hair allowing even application of the chromic composition. Suitably, the chromic composition further comprises a foaming agent. The foaming agent is suitably a surfactant or dispersant, preferably quallaja saponaria or an extract from a pseudomonas or *Bacillus subtilis* culture, or as hereinbefore described. Suitably, the foaming agent is selected such that it does not detract from the colour intensity of the chromic composition and material properties of the binder system.

The chromic composition may be formulated as a hair dye solution, especially a professional hair dye solution. A professional hair dye is intended to be used by hair professionals, usually in a hair salon, where fine control in applying the hair dye to ensure deposition in the appropriate location is required. Suitably, the binder composition comprises a stronger fixative which takes longer to set in place in the hair but reduces or prevents migration of chromic dye between hair fibres, maintaining the designs of hair stylists. Examples of suitable polymers include polyurethanes.

Suitably the chromic composition, when formulated for use as a professional or salon dye, has a viscosity of 1 kcP to 5 kcP. A chromic composition formulated for personal use suitably has a viscosity of 50 cP to 1 kcP.

The chromic composition in a form suitable for use as a salon or professional is preferably applied with an applicator by a trained professional in a salon environment.

The invention also provides a novel applicator comprising a reservoir for a chromic composition, a nozzle in fluid communication with the reservoir, a pump for providing and/or regulating flow of the composition from the reservoir to the nozzle, a housing, and optionally, a source of UV light and light transmission means for transmitting UV light to the nozzle and being adapted to irradiate the dispensed chromic composition.

The chromic composition may be "fixed" once applied to the hair by any suitable means, for example by application of UV light or energy transfer through heating or cooling, for example using a hair dryer, or by infra-red. In heating the composition, the composition may be dried, that is removal of a volatile component to leave a solid residue, or cured, that is by reacting components chemically.

The chromic composition according to the invention for use with a UV applicator comprises a UV polymerisable component as a component of the binder composition or may include a component which may be dried upon application to the hair. A UV curable chromic composition according to the invention suitably further comprises a photoinitiator which, when activated by UV light from the applicator, initiates a free radical reaction in the formulation and suitably the binder composition comprises a UV curable acrylate, for example a polyacrylate or triacrylate to provide cross-linking. Suitably, the photoinitiator has a low toxicity and known photoinitiators may be used, for example Irgacure 2959.

In this case, applicator suitably comprises a source of ultra violet (UV) light and on delivery of the chromic composition to the hair, irradiate the applied composition with UV light to cure it.

The composition suitably has a higher viscosity than compositions formulated and intended for home or personal use. This enables better control colour deposition on the hair and is especially suitable for professional use in a salon. Controlled application allows a film, preferably a uniform film, to be deposited on the surface of the hair.

A dryable or curable chromic composition which is dried or cured using temperature change, for example heating may be applied using a hair brush, paint brush or other conventional application means or may be applied using an applicator according to the invention. In this case, the applicator need not include a UV source or means for delivering UV to the applied composition. The composition is suitably deposited on the hair, for example by spraying or coating, dried for example by application of heat or by cooling, suitably employing a bristled brush as described above. The procedure is preferably repeated multiple, especially from 2 to 5 times, for example 3 times to allow the chromic composition to build up the chromic composition to provide the desired effect but without clogging the hair together.

For a UV applicator, the pump is suitably electronically controlled. Where employed, the light transmission means is suitably a fibre-optic cable.

Where the applicator is configured to deliver a heat dried chromic composition, the chromic composition is suitably dispensed by a hand-held device, for example a propellant airbrush or by hand-held painting The applicator is adapted to receive a variety of nozzle attachments to provide different effects and for use with different hair types.

In a further embodiment, the invention provides a method of applying a chromic composition, preferably a chromic composition according to the invention, to a substrate, preferably keratinous material, for example hair, comprising providing an applicator adapted to carry a body of chromic composition, and having a dispensing nozzle and a means for conveying the composition to the nozzle and UV irradiating means, according to the invention, the applicator being charged with a chromic composition, locating the nozzle of the applicator adjacent to the substrate, operating the applicator whereby composition is conveyed from the applicator through the nozzle and dispensed on the substrate and irradiating the dispensed composition, thereby to provide a substrate having a chromic composition applied thereto.

Certain safety regulations found in Europe for example REACH, CIRS and CPTA, aim to reduce the level of formaldehyde and paraformaldehyde to provide environmentally cleaner materials. During encapsulation, formaldehyde and/or paraformaldehyde may be employed and carried into the encapsulated product. Preferably, paraformaldehyde and formaldehyde are removed during production of the colour change composition. Suitably, the chromic composition contains less than 0.2% by weight of formaldehyde and paraformaldehyde and desirably is substantially free of these materials.

A composition according to the invention is suitably prepared by mixing the components of the chromic composition together in the desired quantities and ratios. The colour change composition components may be mixed together to form the colour change composition and the binder composition may be mixed together to form a binder composition. The formulated colour-change composition and the formulated binder composition may then be mixed together to form the chromic composition. The components may be mixed by hand or in a batch or continuous process as desired. Suitably, the components may be mixed using process apparatus and conditions known to the skilled formulation chemist or process engineer having regard to the components of the composition.

All percentages and ratios used herein are by weight of the total composition and all measurements made are at 25° C., unless otherwise designated.

The term "keratinous" as used herein, refers to tissue comprising keratin-containing layers disposed as the outermost protective covering of mammals (e.g., humans, dogs, cats, etc.) which includes, but is not limited to, skin, mucosa, lips, hair, toenails, fingernails, cuticles, and the like.

The terms "topical application", "topically", and "topical", as used herein, mean to apply for example spread or spray, the composition of the present invention onto the surface of the keratinous tissue.

The term "dermatologically acceptable," as used herein, means that the compositions or components thereof so described are suitable for use in contact with mammalian keratinous tissue without undue toxicity, incompatibility, instability, allergic response, and the like.

The term "orally acceptable", as used herein, means that the compositions or components thereof so described are suitable for oral ingestion by a mammal without undue toxicity, incompatibility, instability, allergic response, and the like.

The invention is illustrated by the accompanying FIGURES in which:

FIG. 1 shows a perspective view of an applicator according to the invention.

In FIG. 1, the applicator (1) has a reservoir (2) for a chromic composition, a pump (not shown) in a casing (3) for pumping the composition from the reservoir to an outlet or nozzle (4) for dispensing the composition onto a substrate such as hair. The nozzle (4) is in fluid communication with the reservoir (2) and the pump is arranged so as to convey composition to the nozzle and, in a preferred embodiment to provide for modulation or regulation of the rate of flow of the composition in response to user demand. A source of UV light is provided in casing (6) and light transmission means (7), for example optical fibres for transmitting UV light to the nozzle (4) are provided. The UV light is directed towards the hair so as to irradiate the chromic composition dispensed on the hair.

Upon being dispensed, the chromic composition is irradiated by UV light emanating from optical fibre outlets (8). The applicator (1) comprises a housing (9) for the light transmission means (7) to communicate with the outlets (8), The composition may pass from the reservoir (2) to the nozzle (4) through tubing (5) passing through the housing (9). The housing may be of any shape but is suitably longitudinally extending and of an aesthetically pleasing design. For example, the housing (9) may have a generally triangular cross-section with straight or, as shown, curved sides.

The casing (6) may also house electronics and a control chip, for example an arduino chip and a power control module. Power is suitably supplied to the applicator by a mains supply and the housing (9) suitably includes a power input (10). The applicator may be powered by battery (not shown) and the housing (9) may be adapted to accommodate batteries to enable use away from a power supply. The applicator (1) includes a gain switch (11) to control the pump and cable (12) supplies power to the pump. The applicator further includes a gain switch (13) for the UV light source and a power or on/off switch (14). The reservoir (2) may have a removable closure (15) to allow replenishment or replacement of the chromic composition as appropriate. The casing (3) and the casing (6) may be connected by a strut (16) or otherwise mounted on the housing (9).

In a preferred embodiment, the applicator also comprises a screen (not shown) which provides an image of the area of the hair on which the composition is being dispensed to assist the user in controlling the rate of dispensing the composition and the location at which it is dispensed and manipulated by the user.

The applicator (1) is suitably hand-held although automated and/or remote control may be employed.

The invention is illustrated by the following non-limiting examples.

EXAMPLES

Examples of colour change formulations suitable for application to hair and having different product forms and resistance to wash are set out below. The amounts of listed components in these examples are by volume, unless otherwise specified.

In Examples 1 to 6 below, the colour-change component is an aqueous leuco dye. Examples 7 to 12 show compositions of the invention in which the colour change component is an encapsulated aqueous liquid crystal. Example 13 shows a composition of the invention in which the colour-change component is an unsealed liquid crystal in low Mn PDMS Examples 1 to 6—Encapsulated Liquid Crystals Example 1—Liquid Dye/Spray

| Components | Amount |
|---|---|
| poly(maleic anhydride-co-vinyl methyl ether) | 15 |
| ethanolamine | 2 |
| encapsulated leuco dye slurry | 50 |
| polysorbate 20 | 3 |
| perfume | <5% |
| potassium sorbate | 1% |

The composition was applied to hair in accordance with the following protocol.

Hair Wash Protocol

After dying, the hair is made wet with water, then agitated with conventional shampoo (for example Head and Shoulders) for 5 minutes, then washed in warm (40° C.) water until no shampoo is left. The hair is then dried with a conventional hair dryer until no longer wet.

Samples of unwashed and washed hair are kept between each wash and the colour intensity compared. At the point at which the washed hair has very similar colour to the original undyed hair, the dye is considered to be washed out.

Wash out hair chalk is suitably applied by washing and drying the hair, applying the chalk, preferably using a brush as described herein and then dry the hair with a hair dryer and brush out any excess material. The chromic composition remains in the hair until the next wash whereupon it is washed out.

The composition of Example 1 was washed and remained in the hair providing effective colour-change for 2 washes.

Example 2—Mousse

| Components | Amount |
|---|---|
| poly(acrylic acid-co-acrylamide) | 20 |
| citric acid | 2 |
| capryl glucoside | 3 |
| encapsulated leuco dye slurry | 50 |
| perfume | <1 |

The composition was applied to hair which was then successively washed in accordance with the Hair Wash Protocol and remained in the hair providing effective colour-change for 3 washes.

Example 3—Propellable Spray

| Components | Amount |
|---|---|
| polyvinylpyrrolidone | 24 |
| encapsulated leuco dye slurry | 40 |
| dimethyl carbonate | 30 |
| sorbic acid | 1 |
| glyceryl cocoate | 5 |

The composition was applied to hair which was then successively washed in accordance with the Hair Wash Protocol and remained in the hair providing effective colour-change for 1 wash.

Example 4—Salon Applied Gel

| Components | Amount |
| --- | --- |
| Methacrylated gelatin | 30 |
| IRGACURE 2959 | 5 |
| polysorbate 80 | 5 |
| encapsulated leuco dye slurry | 50 |
| carylyl glycol | 5 |
| perfume chemicals | 4 |

The composition was applied to hair using a UV applicator device which was then successively washed in accordance with the Hair Wash Protocol and remained in the hair providing effective colour-change for 6 washes.

Example 5

| Components | Amount |
| --- | --- |
| acrylic terpolymer | 30 |
| encapsulated leuco dye slurry | 50 |
| tea tree oil | 1 |
| Alkali swellable emulsion (ASE) | 15 |
| guar gum | 3 |
| perfume chemicals | 1 |

Example 6—Chalk

| Components | Amount |
| --- | --- |
| high molecular weight (Mn > 2000) ethyl acrylamide | 30 |
| encapsulated leuco dye slurry | 50 |
| citric acid | 3 |
| perfume chemicals | 3 |

Examples 7 to 12—Encapsulated Liquid Crystals

Example 7—Liquid Dye/Spray

| Components | Amount |
| --- | --- |
| poly(maleic anhydride-co-vinyl methyl ether) | 15 |
| ethanolamine | 2 |
| encapsulated liquid crystal slurry | 50 |
| polysorbate 20 | 3 |
| perfume | <5% |
| potassium sorbate | 1% |

The composition was applied to hair which was then successively washed in accordance with the Hair Wash Protocol and remained in the hair providing effective colour-change for 2 washes.

Example 8—Mousse

| Components | Amount |
| --- | --- |
| poly(acrylic acid-co-acrylamide) | 20 |
| citric acid | 2 |
| capryl glucoside | 3 |
| encapsulated liquid crystal slurry | 50 |
| perfume | <1 |

The composition was applied to hair which was then successively washed in accordance with the Hair Wash Protocol and remained in the hair providing effective colour-change for 3 washes.

Example 9—Propellable Spray

| Components | Amount |
| --- | --- |
| polyvinylpyrrolidone | 24 |
| encapsulated liquid crystal slurry | 40 |
| dimethyl carbonate | 30 |
| sorbic acid | 1 |
| glyceryl cocoate | 5 |

The composition was applied to hair which was then successively washed in accordance with the Hair Wash Protocol and remained in the hair providing effective colour-change for 1 wash.

Example 10—Salon Applied Gel

| Components | Amount |
| --- | --- |
| Methacrylated gelatin | 30 |
| IRGACURE 2959 | 5 |
| polysorbate 80 | 5 |
| encapsulated liquid crystal dye slurry | 50 |
| carylyl glycol | 5 |
| perfume chemicals | 4 |

The composition was applied to hair using a UV applicator device which was then successively washed in accordance with the Hair Wash Protocol and remained in the hair providing effective colour-change for 6 washes.

Example 11

| Components | Amount |
| --- | --- |
| acrylic terpolymer | 30 |
| encapsulated liquid crystal dye slurry | 50 |
| tea tree oil | 1 |
| ASE | 15 |
| guar gum | 3 |
| perfume chemicals | 1 |

Example 12—Chalk

| Components | Amount |
| --- | --- |
| high molecular weight (Mn > 2000) ethyl acrylamide | 30 |
| encapsulated liquid crystal dye slurry | 50 |
| citric acid | 3 |
| perfume chemicals | 3 |

Examples 13—Unsealed Liquid Crystal (in Low Mn PDMS): Salon Applied Gel

| Components | Amount |
| --- | --- |
| Methacrylated gelatin | 30 |
| IRGACURE 2959 | 5 |
| polysorbate 80 | 5 |
| unsealed liquid crystal | 50 |
| carylyl glycol | 5 |
| perfume chemicals | 4 |

The composition was applied to hair using a UV applicator device which was then successively washed in accordance with the Hair Wash Protocol and remained in the hair providing effective colour-change for 6 washes.

Example 14

A composition according to the invention was formulated as a hair dye whose colour changes with response to temperature, creating a vivid effect with high aesthetic. The colour change characteristics were tested with external influence being provided from i) the ambient temperature of the environment and ii) contact of skin.

Environmental:

Infra-red thermographic data was collected to find differences in the temperatures of a surface, including hair and skin, utilising a controlled environment chamber in which temperature, whether by convection or irradiation, wind speed, UV and humidity are controlled. This data was used to tune the formulation to display a thermochromic effect at desired temperature points with a bandwidth to mimic different scenarios. The scenarios were:

summer heat vs winter cool temperatures
indoor vs outdoor temperatures
day vs night temperatures Skin Contact:

Thermographic data and published thermal physiological research literature, was used to tune the formulation to display a thermochromic effect upon contact with skin in various environmental conditions.

Colour:

Compositions of the invention were formulated to provide two, three and four colour changes, respectively dichromic, trichromic and tetrachromic, were prepared by formulating materials to provide the desired sequence of colour change and then tailoring the vibrancy of the colour and contrast between the colours of the chromic composition. The compositions provided vivid colours and colour change and provided uniform colouration uniform across the hair.

2. Construction of Colour Change Sequence:

The composition was prepared so as to provide desired colour change sequences and the desired thermochromic effects were provided by using thermographic data previously collected. Colours were selected so that complementary and contrasting colours were placed adjacent to each other in sequence together to create optimal, striking and appealing differentiations between each colour. An example of sequences can be seen below:

a. Tetrachromic (four colours):
    i. $15° C. < T_{Hair} < 20° C.$=black
    ii. $20° C. < T_{Hair} < 23° C.$=red
    iii. $23° C. < T_{Hair} < 28° C.$=orange
    iv. $30° C. < T_{Hair}$=yellow
  b. Trichromic (three colours):
    i. $20° C. < T_{Hair} < 23° C.$=red
    ii. $23° C. < T_{Hair} < 28° C.$=orange
    iii. $30° C. < T_{Hair}$=yellow
  c. Dichromic (two colours):
    i. $T_{Hair} < 29° C.$=black
    ii. $29° C. < T_{Hair}$=red 3. Optimisation of the Colour Vibrancy:

The Thermochromic colour tone was developed from conventional pastel colours to create a more brilliant tone (brighter, more reflective) by successive reformulations with varying proportions of dye components. The results of this method were a more intense and more vivid colour, with a more striking aesthetic effect and contrast between different colours of the chromic composition and especially the contrast between black and red. Additive dyes were selected and reformulated based on their refractive indices, such that molecules with more similar indices had brighter colours.

Results

The results show that compositions of the invention may be formulated and tuned to provide a desired thermochromic effect to display colour changes to convey a concept story. For example, a black to red change gradually during the summer or instantly when temperatures are above 28 degrees, or black to blue instant change when the wind chill below 15 degrees contacts the hair.

We conducted experiments on hair to select the bandwidth of temperature in which the colour change effect takes place for each concept scenario.

Lengthening and shortening the time it takes for each colour effect to respond may be tuned by adding a dopant that delays or speeds up the chemical interaction which produces a colour change over short or long temperature gradients.

The invention claimed is:

1. A chromic composition product adapted for application to a substrate, the substrate including human hair, nails, or skin, comprising a reversible colour-change composition which comprises a colour-change component selected from a leuco dye and a liquid crystal, and a binder composition comprising a fixative, a carrier and optionally a rheology modifier wherein the fixative comprises a polymer having one or more monomeric units selected from acrylic acid, methacrylic acid, hydroxyethyl methacrylic acid, alkyl $C_1$ to $C_4$, methacrylic acid, alkyl $C_1$ to $C_4$, acrylic acid, alkyl $C_1$ to $C_4$, amino acrylic acids, esters of any such acrylic or methacrylic monomers and ethers of any such acrylic or methacrylic monomers, acrylated dimethiconol, alkyl, $C_2$ to $C_8$, amide, polyethylene glycol, polypropylene glycol, polybutylene glycol, $C_2$ to $C_4$ alkylene glycols, maleic anhydride, dimethylaminopropylamine (in polyimide-1), vinyl pyrrolidone (in PVP and polyquaternium-1/11), vinyl alcohol, alkylene polyethylene glycol, alkyl $C_2$ to $C_8$, acrylamide, vinyl caprolactam, vinyl acetate, vinyl methyl ether, crotonic acid, and esters and ethers thereof and methacrylated gelatin, wherein the colour change composition is present in the chromic composition at a level of 10 to 90% by weight, and the range of the liquid crystal is from 10 to 90% by weight.

2. A chromic composition according to claim 1 in which the reversible colour change composition comprises a thermochromic compound and the substrate is keratinous material, hair, or nail.

3. A chromic composition according to claim 1 in which the reversible colour-change composition is thermochromic.

4. A chromic composition according to claim 1 in which the leuco dye or liquid crystal is encapsulated.

5. A chromic composition according to claim 1 in which the colour-change compound comprises a poly-dispersed liquid crystal.

6. A chromic composition according to claim 1 in which the binder composition is present in the chromic composition at a level of 90 to 10% by weight.

7. A chromic composition according to claim 1 in which the chromic composition provides colour-change and is iridescent.

8. A chromic composition according to claim 1 in which the chromic composition provides colour-change and is non-iridescent.

9. A chromic composition according to claim 1 in which the colour change composition comprises two or more colour-change components.

10. A chromic composition according to claim 1 in which the fixative comprises an alkyl ester of a copolymer of vinyl methyl ether and maleic anhydride or maleic acid.

11. A chromic composition according to claim 1 in the form of a spray, a paint, a hair dye, a shampoo, a conditioner, a mousse, wax, gel or solid hair product.

12. A chromic composition according to claim 1 for application to hair in which the reversible colour change composition comprises a thermochromic encapsulated liquid crystal and the fixative comprises:
   i) a polymer having one or more monomeric units selected from acrylic acid, methacrylic acid, hydroxyethyl methacrylic acid, alkyl methacrylic acid, alkyl acrylic acid, alkyl amino acrylic acids, esters of any such acrylic or methacrylic monomers; and
   ii) a glycol selected from polyethylene glycol, polypropylene glycol, polybutylene glycol and a $C_2$ to $C_4$ alkylene glycol.

13. A chromic composition according to claim 1 further comprising a dye.

14. A chromic composition according to claim 1 adapted for application to hair in which the reversible colour change composition comprises a thermochromic encapsulated liquid crystal having a particle size of 5 to 50 microns to impart a vibrant colour to the hair without compromising its feel.

15. A cosmetic product comprising a cosmetic composition and a chromic composition according to claim 1.

16. A method of providing a reversible colour-change substrate adapted to change colour comprising applying to a substrate a chromic product according to claim 1.

17. A method of providing a temporary colour effect to dark hair without subjecting the hair to a lightening pre-treatment comprising applying to the hair a chromic composition according to claim 1 in which the reversible colour change composition comprises a thermochromic encapsulated liquid crystal having a particle size of 5 to 50 microns to impart a vibrant colour to the hair without compromising its feel.

18. A method according to claim 16 in which the substrate is selected from a natural polymer, a synthetic polymer, metal and keratinous tissue.

\* \* \* \* \*